US012778496B2

(12) United States Patent
Shute et al.

(10) Patent No.: US 12,778,496 B2
(45) Date of Patent: Nov. 3, 2026

(54) WEARABLE HEART FAILURE MONITOR

(71) Applicant: Cardiac Pacemakers, Inc., St. Paul, MN (US)

(72) Inventors: Jonathan Bennett Shute, Eagan, MN (US); Bin Mi, Arden Hills, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 247 days.

(21) Appl. No.: 18/631,421

(22) Filed: Apr. 10, 2024

(65) Prior Publication Data

US 2024/0341677 A1 Oct. 17, 2024

Related U.S. Application Data

(60) Provisional application No. 63/458,476, filed on Apr. 11, 2023.

(51) Int. Cl.
*A61B 5/00* (2006.01)
*A61B 5/0205* (2006.01)
(Continued)

(52) U.S. Cl.
CPC .......... *A61B 5/4836* (2013.01); *A61B 5/0022* (2013.01); *A61B 5/0205* (2013.01); *A61B 5/349* (2021.01); *A61B 5/6801* (2013.01); *A61B 5/686* (2013.01); *A61B 5/7275* (2013.01); *A61B 5/742* (2013.01); *A61B 5/1116* (2013.01); *A61B 5/1118* (2013.01); *A61B 2560/0443* (2013.01); *A61B 2560/0462* (2013.01); *A61B 2562/0219* (2013.01)

(58) Field of Classification Search
CPC ... A61B 5/4836; A61B 5/0022; A61B 5/0205; A61B 5/349; A61B 5/6801
See application file for complete search history.

(56) References Cited

U.S. PATENT DOCUMENTS

2020/0178850 A1 * 6/2020 Thakur .................... A61B 7/00

OTHER PUBLICATIONS

Patel, Priyesh A., et al., "Association Between Systolic Ejection Time and Outcomes in Heart Failure by Ejection Fraction", HHS Public Access Author manuscript, Published in final edited form as: Eur J Heart Fail. Jul. 2020 ; 22(7): 1174-1182. doi:10.1002/ejhf.1659.

(Continued)

*Primary Examiner* — Carl H Layno
*Assistant Examiner* — Bryan McAllister Lee
(74) *Attorney, Agent, or Firm* — Nelson Mullins Riley & Scarborough LLP

(57) ABSTRACT

Systems and methods for detecting and managing heart failure are discussed. A medical-device system receives heart sound information sensed from the patient, generates a heart sound metric using the received heart sound information, and generate a heart failure indicator indicating whether the patient has a heart failure with preserved ejection fraction (HFpEF) or a heart failure with reduced ejection fraction (HFrEF) based at least in part on the heart sound metric. The medical-device system can detect a transition from HFpEF to HFrEF. A therapy circuit can deliver or adjust a heart failure therapy in response to the detected transition from HFpEF to HFrEF.

20 Claims, 6 Drawing Sheets

(51) Int. Cl.
*A61B 5/11* (2006.01)
*A61B 5/349* (2021.01)

(56) References Cited

OTHER PUBLICATIONS

Van Riet, Evelien E.S., et al., "Prevalence of unrecognized heart failure in older persons with shortness of breath on exertion", European Journal of Heart Failure (2014) 16, 772-777 doi:10.1002/ejhf.110.

* cited by examiner

WEARABLE HEART FAILURE MONITOR

CLAIM OF PRIORITY

This application claims the benefit of U.S. Provisional Application No. 63/458,476 filed on Apr. 11, 2023, which is hereby incorporated by reference in its entirety.

TECHNICAL FIELD

This document relates generally to medical devices, and more particularly, to systems, devices and methods for detecting and managing heart failure.

BACKGROUND

Congestive heart failure (CHF) is a leading cause of death in the United States and globally. CHF is the loss of pumping power of the heart, and may affect left heart, right heart, or both sides of the heart, and result in the inability to deliver enough blood to meet the demands of peripheral tissues. CHF patients typically have enlarged heart with weakened cardiac muscles, resulting in reduced contractility and poor cardiac output of blood. CHF may be treated by drug therapy, or by an implantable medical device (IMD) such as for providing electrostimulation therapy. Although usually a chronic condition, CHF may occur suddenly.

Heart failure with preserved ejection fraction (HFpEF) and heart failure with reduced ejection fraction (HFrEF) are two major types of heart failures related to ejection fraction (EF). HFpEF, also known as diastolic heart failure, accounts for more than 50% of clinical heart failure cases. HFpEF occurs due to insufficient filling of the left ventricle with blood. The ventricle does not relax properly and thus is unable to fill with blood properly during the diastole, such as due to stiff and or thickened left ventricular (LV) heart muscles. However, patients with HFpEF generally have normal or near normal EF (e.g., greater than 50%). Coronary artery disease, high blood pressure, aortic stenosis, hypertrophic cardiomyopathy and pericardial disease are major causes of HFpEF. HFrEF, also known as systolic heart failure, occurs when the left ventricle fails to pump an adequate amount of oxygen-rich blood to the body, resulting a lower than normal EF (e.g., less than 40%). Heart attacks, coronary artery disease, high blood pressure, mitral regurgitation, viral myocarditis and aortic stenosis are the major cause of HFrEF.

Some IMDs are capable of monitoring CHF patients and detect events leading to worsening heart failure (WHF). These IMDs may include sensors to sense physiological signals from a patient. Frequent patient monitoring may help reduce heart failure hospitalization. Identification of patient at an elevated risk of developing WHF, such as heart failure decompensation, may help ensure timely treatment and improve prognosis and patient outcome. Identifying and safely managing the patients at elevated risk of WHF may avoid unnecessary medical interventions, hospitalization, and thereby reduce healthcare cost.

An IMD may contain electronic circuitry, such as a pulse generator, to generate and deliver electrostimulation to excitable tissues or organs, such as a heart. The electrostimulation may help restore or improve a CHF patient's cardiac performance, or rectify cardiac arrhythmias. One example of such electrostimulation therapy is resynchronization therapy (CRT) for correcting cardiac dyssynchrony in CHF patients.

SUMMARY

Frequent monitoring of CHF patients and timely detection of intrathoracic fluid accumulation or other events indicative of heart failure decompensation status may help prevent WHF in CHF patients, hence reducing cost associated with heart failure hospitalization.

Ambulatory medical devices for monitoring heart failure patient may include implantable medical devices (IMD), subcutaneous medical devices, wearable medical devices or other external medical devices. An ambulatory medical device may be coupled to one or more physiological sensors to sense electrical activity and mechanical function of the heart. The ambulatory medical device may optionally deliver therapy, such as electrical stimulation pulses, to the patient to restore or improve patient cardiac function. Some of these devices may provide diagnostic features, such as using transthoracic impedance or other sensor signals. For example, fluid accumulation in the lungs decreases the transthoracic impedance due to the lower resistivity of the fluid than air in the lungs. The fluid accumulation may also elevate ventricular filling pressure, resulting in a louder S3 heart sound. Additionally, fluid accumulation in the lungs may irritate the pulmonary system and leads to decrease in tidal volume and increase in respiratory rate.

Identification of patient at an elevated risk of WHF may help ensure timely intervention such as device therapy or drug therapy, thereby improving the prognosis and patient outcome. On the other hand, identifying and safely managing patients with low risk of WHF may avoid unnecessary medical interventions, thereby reducing healthcare cost. Desired performance of WHF risk stratification may include one or more of a high sensitivity, a high specificity, a high positive predictive value (PPV), or a negative predictive value (NPV). The sensitivity represents an accuracy of identifying patients with relatively a high risk of WHF. The specificity represents an accuracy of identifying patients with relatively a low risk of WHF.

Echocardiography and biomarker tests (e.g., natriuretic peptide tests) are standard approaches to diagnose heart failure. The ratio of early diastolic mitral inflow velocity to early diastolic mitral annulus velocity (also known as E/e' ratio), estimated using tissue Doppler echocardiography, has been used to evaluate the left ventricular (LV) filling pressure and LV stiffness, and to diagnose heart failure such as HFpEF. B-type natriuretic peptide (BNP) or N-terminal-pro-BNP (NT-pro-BNP)) is a protein secreted from heart muscles during hemodynamic overload. It can reflect LV end-diastolic wall stress, and has been used as a marker for the evaluation of HFpEF and assessment of prognosis. Clinically, HFpEF may also be diagnosed using cardiac catheterization during exertion to detect an exaggerated increase in LV filling pressure from baseline at rest, a hallmark signature of HFpEF.

Although these conventional echocardiography and/or biomarker tests are generally effective in diagnosing HFrEF, they can be more challenging to produce consistent and reliable outcome in diagnosing HFpEF. For example, some patients with invasively proven HFpEF nevertheless displayed normal NT-pro-BNP levels. The E/e' ratio used as a surrogate for filling pressure, although a good indicator of large pressure differences, it may not be a reliable indicator of smaller changes in filling pressure (e.g., changes with exercise). Cardiac catheterization during exertion (to detect increase in LV filling pressure) can be difficult to deploy as a screening tool in a clinical setting. Furthermore, HFpEF can be clinically complicated with a variety of pathophysiological presentations other than diastolic dysfunction including, for example, longitudinal systolic dysfunction, chronotropic incompetence, autonomic dysfunction, endothelial dysfunction, pulmonary hypertension, abnormal atrioventricular coupling, skeletal muscle abnormalities, information, arterial stiffness, extra-cardiac causes of volume overload, among others. As such, HFpEF patients can be underdiagnosed or misdiagnosed, and do not get properly identified until they have had multiple episodes of acute decompensated heart failure (ADHF) with new or worsening signs and symptoms leading to hospitalization or an emergency department visit. For at least the above reasons, the present inventors have recognized an unmet need for systems and methods for diagnosing CHF, particularly HFpEF, and managing patients with such conditions.

This document discusses, among other things, a patient management system for detecting and managing heart failure, particularly HFpEF or HFrEF. In accordance with an embodiment as described herein, a medical-device system can receive from the patient physiological information including heart sound information. Based at least in part on a heart sound metric generated from the heart sound information, the medical-device system can generate a heart failure indicator indicating whether the patient has a HFpEF or HFrEF. The medical-device system can detect a transition from HFpEF to HFrEF. The medical-device system includes a therapy circuit that can deliver or adjust a heart failure therapy in response to the detected transition from HFpEF to HFrEF.

Example 1 is a medical-device system for detecting and managing heart failure, the medical-device system comprising: a data receiver circuit configured to receive heart sound information sensed from a patient, the heart sound information including one or more of S1, S2, S3, or S4 heart sound components; and a heart failure detector circuit configured to: generate a heart sound metric using the received heart sound information; and generate a heart failure indicator indicating whether the patient has a heart failure with preserved ejection fraction (HFpEF) or a heart failure with reduced ejection fraction (HFrEF) based at least in part on the generated heart sound metric.

In Example 2, the subject matter of Example 1 optionally includes a wearable device that includes an accelerometer and the heart failure detector circuit, the accelerometer configured to sense the heart sound information from the patient.

In Example 3, the subject matter of any one or more of Examples 1-2 optionally include, wherein the heart sound metric includes an S3 intensity metric, wherein the heart failure detector circuit is configured to generate the heart failure indicator indicating a presence of HFpEF when the S3 intensity metric exceeds an S3 threshold.

In Example 4, the subject matter of any one or more of Examples 1-3 optionally include, wherein the data receiver circuit is configured to receive the heart sound information sensed from the patient when the patient is in a specific posture or engaged in a specific physical activity.

In Example 5, the subject matter of Example 4 optionally includes a posture sensor configured to detect the specific posture in the patient.

In Example 6, the subject matter of any one or more of Examples 4-5 optionally include an activity sensor configured to detect the patient engagement in the specific physical activity.

In Example 7, the subject matter of any one or more of Examples 4-6 optionally include, wherein the received heart sound information includes first heart sound information when the patient is in a resting state and second heart sound information when the patient in a physically active state, wherein the heart failure detector circuit is configured to: generate a first heart sound metric from the first heart sound information and a second heart sound metric from the second heart sound information; and generate the heart failure indicator based at least in part on a change or a rate of change from the first heart sound metric to the second heart sound metric.

In Example 8, the subject matter of Example 7 optionally includes, wherein the first heart sound metric includes a first S3 intensity metric when the patient is in the resting state, and the second heart sound metric includes a second S3 intensity metric when the patient in the physically active state, wherein the heart failure detector circuit is configured to generate the heart failure indicator indicating a presence of HFpEF in response to a difference between the first and the second S3 intensity metrics exceeding a threshold.

In Example 9, the subject matter of any one or more of Examples 1-8 optionally include, wherein the heart sound metric includes an S1 timing relative to a fiducial point, the S1 timing indicative of a pre-ejection period, wherein the heart failure detector circuit is configured to generate the heart failure indicator indicating (i) a presence of HFrEF in response to the S1 timing relative to the fiducial point exceeding a threshold, and (ii) a presence of HFpEF in response to the S1 timing relative to the fiducial point falling below the threshold.

In Example 10, the subject matter of Example 9 optionally includes, wherein the data receiver circuit is further configured to receive cardiac electrical activity information, wherein the heart failure detector circuit is configured to recognize, from the received cardiac electrical activity information, the fiducial point using a QRS complex within a cardiac cycle preceding the S1 component.

In Example 11, the subject matter of any one or more of Examples 1-10 optionally include, wherein the heart sound metric includes a heart sound-based systolic time interval between a QRS complex in a cardiac electrical signal and an S2 heart sound component with a cardiac cycle, wherein the heart failure detector circuit is configured to generate the heart failure indicator indicating (i) a presence of HFrEF in response to the heart sound-based systolic time interval falling below a threshold, and (ii) a presence of HFpEF in response to the heart sound-based systolic time interval exceeding the threshold.

In Example 12, the subject matter of any one or more of Examples 1-11 optionally include, wherein the heart sound metric includes an S1 to S2 time interval indicative of a left ventricular ejection time, wherein the heart failure detector circuit is configured to generate the heart failure indicator indicating (i) a presence of HFrEF in response to the S1 to S2 time interval falling below a threshold, and (ii) a presence of HFpEF in response to the S1 to S2 time interval exceeding the threshold.

In Example 13, the subject matter of any one or more of Examples 1-12 optionally include, wherein the heart sound metric includes a heart sound-based diastolic time interval between S2 and a subsequent QRS complex in a cardiac electrical signal, wherein the heart failure detector circuit is configured to generate the heart failure indicator indicating (i) a presence of HFrEF in response to the heart sound-based diastolic time interval falling below a threshold, and (ii) a presence of HFpEF in response to the heart sound-based diastolic time interval exceeding the threshold.

In Example 14, the subject matter of any one or more of Examples 1-13 optionally include, wherein the heart failure detector circuit is configured to generate a trend of the heart sound metric over time, and to detect an indicator of HFpEF to HFrEF transition based at least in part on the trended heart sound metric.

In Example 15, the subject matter of Example 14 optionally includes a therapy circuit configured to initiate or adjust a heart failure therapy in response to the detected indicator of HFpEF to HFrEF transition.

Example 16 is a method of detecting and managing heart failure using a medical-device system, the method comprising: receiving heart sound information sensed from a patient, the heart sound information including one or more of S1, S2, S3, or S4 heart sound components; generating a heart sound metric using the received heart sound information; and generating a heart failure indicator indicating whether the patient has a heart failure with preserved ejection fraction (HFpEF) or a heart failure with reduced ejection fraction (HFrEF) based at least in part on the generated heart sound metric.

In Example 17, the subject matter of Example 16 optionally includes, wherein the heart sound metric includes an S3 intensity metric, wherein generating the heart failure indicator includes an indicator indicating a presence of HFpEF when the S3 intensity metric exceeds an S3 threshold.

In Example 18, the subject matter of any one or more of Examples 16-17 optionally include: sensing a posture or a physical activity state of the patient using an ambulatory sensor; and sensing the heart sound information using an accelerometer when the sensed posture or the sensed physical activity satisfies a condition.

In Example 19, the subject matter of Example 18 optionally includes, wherein sensing the heart sound information includes sensing first heart sound information when the patient is in a resting state and sensing second heart sound information when the patient in a physically active state, wherein generating the heart sound metric includes generating a first heart sound metric from the first heart sound information and a second heart sound metric from the second heart sound information, wherein generating the heart failure indicator is based at least in part on a change or a rate of change from the first heart sound metric to the second heart sound metric.

In Example 20, the subject matter of Example 19 optionally includes, wherein the first heart sound metric includes a first S3 intensity metric when the patient is in the resting state, and the second heart sound metric includes a second S3 intensity metric when the patient in the physically active state, wherein generating the heart failure indicator includes an indicator indicating a presence of HFpEF in response to a difference between the first and the second S3 intensity metrics exceeding a threshold.

In Example 21, the subject matter of any one or more of Examples 16-20 optionally include, wherein the heart sound metric includes a cardiac timing interval representing at least one of a pre-ejection period, a systolic time interval, a left ventricular ejection time, or diastolic time interval, wherein generating the heart failure indicator includes an indicator indicating a presence of HFpEF or a presence of HFrEF based on a comparison of the cardiac timing interval to a threshold.

In Example 22, the subject matter of any one or more of Examples 16-21 optionally include: detecting an indicator of HFpEF to HFrEF transition based at least in part on a trend of the heart sound metric; and initiating or adjusting a heart failure therapy in response to the detected indicator of HFpEF to HFrEF transition.

Various embodiments described herein may help improve the medical technology of device-based heart failure patient management, particularly computerized diagnosis of HFpEF and monitoring of progression of HFpEF to HFrEF. Compared to conventional echocardiography or cardiac catheterization-based approaches, the heart sound-based diagnostics, such as S3 heart sound intensity or various cardiac timing intervals as described in this document, may improve the accuracy of detecting HF events and tracking HF progression, particularly clinically underdiagnosed HFpEF and/or progression to HFrEF. The heart sound information can be collected using noninvasive, wearable sensors in an ambulatory setting during the patient's daily life, and is easier to deploy than conventional cardiac catheterization during exercise in a clinical setting. By using ambulatory (e.g., wearable) devices equipped with sensors such as heart sound sensors, the timely and reliable diagnosis of HFpEF can be achieved with little to no additional cost. With the improved HFpEF diagnostics, hospitalization and healthcare costs associated with patient management can be reduced. Moreover, the systems, devices, and methods discussed herein also allow for more efficient device memory usage, such as by storing heart sound information that is clinically more relevant to HFpEF diagnostics. As fewer false positive detections of heart failure events are provided, device battery life may be extended; fewer unnecessary drugs and procedures may be scheduled, prescribed, or provided. Therapy titration, such as electrostimulation parameter adjustment, may not only improve therapy efficacy and patient outcome, but may also save device power. As such, overall system cost savings may be realized.

Although the discussion in this document focuses WHF risk assessment, this is meant only by way of example and not limitation. It is within the contemplation of the inventors, and within the scope of this document, that the systems, devices, and methods discussed herein may also be used to detect, and alert occurrence of, cardiac arrhythmias, syncope, respiratory disease, or renal dysfunctions, among other medical conditions. Additionally, although systems and methods are described as being operated or exercised by clinicians, the entire discussion herein applies equally to organizations, including hospitals, clinics, and laboratories, and other individuals or interests, such as researchers, scientists, universities, and governmental agencies, seeking access to the patient data.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting and managing heart failure in a patient. A medical-device system receives heart sound information sensed from the patient, generates a heart sound metric using the received heart sound information, and generate a heart failure indicator indicating whether the patient has a heart failure with preserved ejection fraction (HFpEF) or a heart failure with reduced ejection fraction (HFrEF) based at least in part on the heart sound metric. The medical-device system can detect a transition from HFpEF to HFrEF. A therapy circuit can deliver or adjust a heart failure therapy in response to the detected transition from HFpEF to HFrEF.

Figure 1:
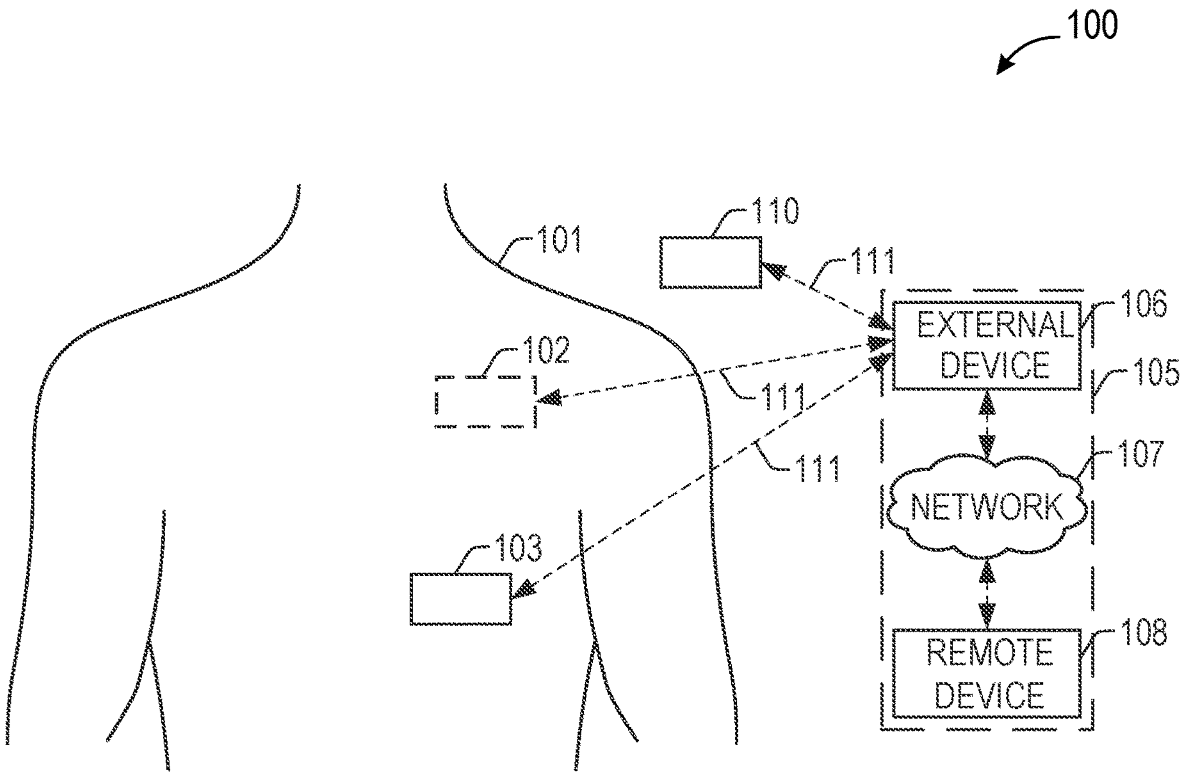
FIG. 1 illustrates generally an example of a patient management system and portions of an environment in which the system may operate.

FIG. 1 illustrates generally an example patient management system 100 and portions of an environment in which the patient management system 100 may operate. The patient management system 100 can perform a range of activities, including remote patient monitoring and diagnosis of a disease condition. Such activities can be performed proximal to a patient 101, such as in a patient home or office, through a centralized server, such as in a hospital, clinic, or physician office, or through a remote workstation, such as a secure wireless mobile computing device.

The patient management system 100 may include one or more ambulatory medical devices, an external system 105, and a communication link 111 providing for communication between the one or more ambulatory medical devices and the external system 105. The one or more ambulatory medical devices may include an implantable medical device (IMD) 102, a wearable medical device (WMD) 103, or one or more other implantable, leadless, subcutaneous, external, wearable, or ambulatory medical devices configured to monitor, sense, or detect information from, determine physiological information about, or provide one or more therapies to treat various conditions of the patient 101, such as one or more cardiac or non-cardiac conditions (e.g., dehydration, sleep disordered breathing, etc.).

In an example, the IMD 102 may include one or more traditional cardiac rhythm management devices implanted in a chest of a patient, having a lead system including one or more transvenous, subcutaneous, or non-invasive leads or catheters to position one or more electrodes or other sensors (e.g., a heart sound sensor) in, on, or about a heart or one or more other position in a thorax, abdomen, or neck of the patient 101. In another example, the IMD 102 may include a monitor implanted, for example, subcutaneously in the chest of patient 101, the IMD 102 including a housing containing circuitry and, in certain examples, one or more sensors, such as a temperature sensor, etc.

The IMD 102 may include an assessment circuit configured to analyze specific physiological information of the patient 101, or to determine one or more conditions or provide information or an alert to a user, such as the patient 101 (e.g., a patient), a clinician, or one or more other caregivers or processes. In an example, the IMD 102 can be an implantable cardiac monitor (ICM) configured to collected cardiac information, optionally along with other physiological information, from the patient. The IMD 102 can alternatively or additionally be configured as a therapeutic device configured to treat one or more medical conditions of the patient 101. The therapy can be delivered to the patient 101 via the lead system and associated electrodes or using one or more other delivery mechanisms. The therapy may include delivery of one or more drugs to the patient 101, such as using the IMD 102 or one or more of the other ambulatory medical devices, etc. In some examples, therapy may include cardiac resynchronization therapy for rectifying dyssynchrony and improving cardiac function in heart failure patients. In other examples, the IMD 102 may include a drug delivery system, such as a drug infusion pump to deliver drugs to the patient for managing arrhythmias or complications from arrhythmias, hypertension, or one or more other physiological conditions. In other examples, the IMD 102 may include one or more electrodes configured to stimulate the nervous system of the patient or to provide stimulation to the muscles of the patient airway, etc.

The WMD 103 may include one or more wearable or external medical sensors or devices (e.g., automatic external defibrillators (AEDs), Holter monitors, patch-based devices, smart watches, smart accessories, wrist- or finger-worn medical devices, such as a finger-based photoplethysmography sensor, etc.).

In an example, the IMD 102 or the WMD 103 may include or be coupled to an implantable or wearable sensor to sense a heart sound signal, and include a heart sound recognition circuit to recognize one or more heart sound components such as S1, S2, S3, or S4. Also included in the IMD 102 or the WMD 103 is a heart sound-based event detector circuit that can detect a physiological event (e.g., a cardiac arrhythmia episode, or a heart failure status such as HFpEF or HFrEF) based at least on a heart sound metric of the detected one or more heart sound component. Examples of such heart sound metric may include an amplitude, or timing of the heart sound component within a cardiac cycle relative to a fiducial point. In some examples, at least a portion of the heart sound recognition circuit and/or the heart sound-based event detector circuit may be implemented in and executed by the external system 105.

In some examples, the IMD 102 or the WMD 103 can detect and manage heart failure using heart sound information sensed from the patient 101. The IMD 102 or the WMD 103 can generate a heart sound metric, and generate a heart failure indicator indicating whether the patient has a HFpEF or HFrEF based at least in part on the generated heart sound metric. In some examples, the IMD 102 or the WMD 103 can trend the heart sound metric over time to detect a transition from HFpEF to HFrEF. A heart failure therapy can be delivered in response to the detected transition from HFpEF to HFrEF.

The external system 105 may include a dedicated hardware/software system, such as a programmer, a remote server-based patient management system, or alternatively a system defined predominantly by software running on a standard personal computer. The external system 105 can manage the patient 101 through the IMD 102 or one or more other ambulatory medical devices connected to the external system 105 via a communication link 111. In other examples, the IMD 102 can be connected to the WMD 103, or the WMD 103 can be connected to the external system 105, via the communication link 111. This may include, for example, programming the IMD 102 to perform one or more of acquiring physiological data, performing at least one self-diagnostic test (such as for a device operational status), analyzing the physiological data, or optionally delivering or adjusting a therapy for the patient 101. Additionally, the external system 105 can send information to, or receive information from, the IMD 102 or the WMD 103 via the communication link 111. Examples of the information may include real-time or stored physiological data from the patient 101, diagnostic data, such as detection of patient hydration status, hospitalizations, responses to therapies delivered to the patient 101, or device operational status of the IMD 102 or the WMD 103 (e.g., battery status, lead impedance, etc.). The communication link 111 can be an inductive telemetry link, a capacitive telemetry link, or a radio-frequency (RF) telemetry link, or wireless telemetry based on, for example, "strong" Bluetooth or IEEE 802.11 wireless fidelity "Wi-Fi" interfacing standards. Other configurations and combinations of patient data source interfacing are possible.

The external system 105 may include an external device 106 in proximity of the one or more ambulatory medical devices, and a remote device 108 in a location relatively distant from the one or more ambulatory medical devices, in communication with the external device 106 via a communication network 107. Examples of the external device 106 may include a medical device programmer. The remote device 108 can be configured to evaluate collected patient or patient information and provide alert notifications, among other possible functions. In an example, the remote device 108 may include a centralized server acting as a central hub for collected data storage and analysis. The server can be configured as a uni-, multi-, or distributed computing and processing system. The remote device 108 can receive data from multiple patients. The data can be collected by the one or more ambulatory medical devices, among other data acquisition sensors or devices associated with the patient 101. The server may include a memory device to store the data in a patient database. The server may include an alert analyzer circuit to evaluate the collected data to determine if specific alert condition is satisfied. Satisfaction of the alert condition may trigger a generation of alert notifications, such to be provided by one or more human-perceptible user interfaces. In some examples, the alert conditions may alternatively or additionally be evaluated by the one or more ambulatory medical devices, such as the implantable medical device. By way of example, alert notifications may include a Web page update, phone or pager call, E-mail, SMS, text or "Instant" message, as well as a message to the patient and a simultaneous direct notification to emergency services and to the clinician. Other alert notifications are possible. The server may include an alert prioritizer circuit configured to prioritize the alert notifications. For example, an alert of a detected physiological event can be prioritized using a similarity metric between the physiological data associated with the detected physiological event to physiological data associated with the historical alerts.

The remote device 108 may additionally include one or more locally configured clients or remote clients securely connected over the communication network 107 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning. In addition to generating alert notifications, the remote device 108, including the server and the interconnected clients, may also execute a follow-up scheme by sending follow-up requests to the one or more ambulatory medical devices, or by sending a message or other communication to the patient 101 (e.g., the patient), clinician or authorized third party as a compliance notification.

The communication network 107 can provide wired or wireless interconnectivity. In an example, the communication network 107 can be based on the Transmission Control Protocol/Internet Protocol (TCP/IP) network communication specification, although other types or combinations of networking implementations are possible. Similarly, other network topologies and arrangements are possible.

One or more of the external device 106 or the remote device 108 can output the detected physiological events to a system user, such as the patient or a clinician, or to a process including, for example, an instance of a computer program executable in a microprocessor. In an example, the process may include an automated generation of recommendations for anti-arrhythmic therapy, or a recommendation for further diagnostic test or treatment. In an example, the external device 106 or the remote device 108 may include a respective display unit for displaying the physiological or functional signals, or alerts, alarms, emergency calls, or other forms of warnings to signal the detection of arrhythmias. In some examples, the external system 105 may include an external data processor configured to analyze the physiological or functional signals received by the one or more ambulatory medical devices, and to confirm or reject the detection of arrhythmias. Computationally intensive algorithms, such as machine-learning algorithms, can be implemented in the external data processor to process the data retrospectively to detect cardia arrhythmias.

Portions of the one or more ambulatory medical devices or the external system 105 can be implemented using hardware, software, firmware, or combinations thereof. Portions of the one or more ambulatory medical devices or the external system 105 can be implemented using an application-specific circuit that can be constructed or configured to perform one or more functions or can be implemented using a general-purpose circuit that can be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. "Sensors" may include electronic circuits configured to receive information and provide an electronic output representative of such received information.

The therapy device 110 can be configured to send information to or receive information from one or more of the ambulatory medical devices or the external system 105 using the communication link 111. In an example, the one or more ambulatory medical devices, the external device 106, or the remote device 108 can be configured to control one or more parameters of the therapy device 110. The external system 105 can allow for programming the one or more ambulatory medical devices and can receives information about one or more signals acquired by the one or more ambulatory medical devices, such as can be received via a communication link 111. The external system 105 may include a local external implantable medical device programmer. The external system 105 may include a remote patient management system that can monitor patient status or adjust one or more therapies such as from a remote location.

Figure 2:
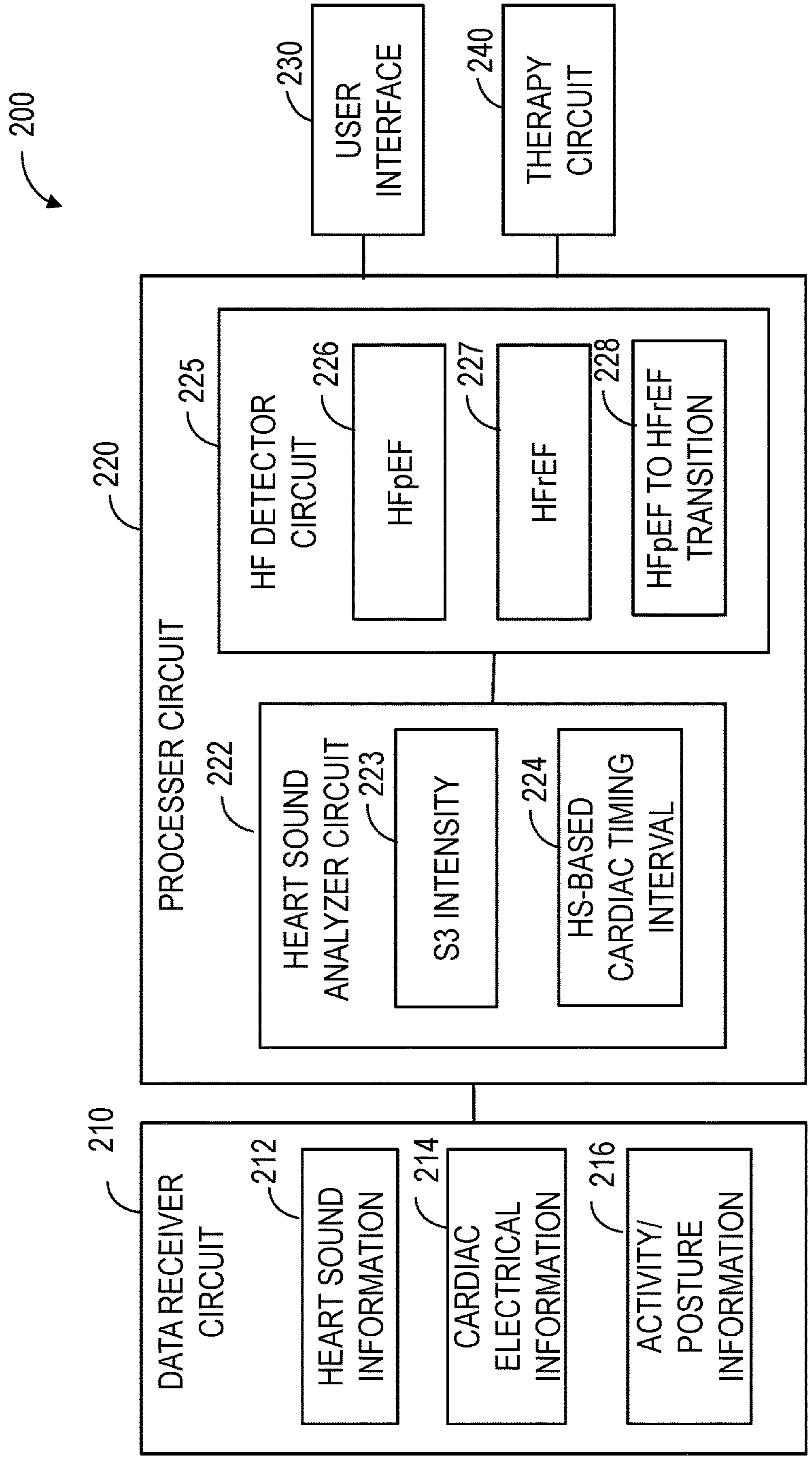
FIG. 2 illustrates generally an example of a heart failure monitor system configured to detect a heart failure status in a patient, such as a heart failure with preserved ejection fraction (HFpEF) or a heart failure with reduced ejection fraction (HFrEF).

FIG. 2 illustrates generally an example of a heart failure monitor system 200 configured to detect a heart failure status, such as HFpEF or HFrEF, from a patient. The heart failure monitor system 200 may include one or more of a data receiver circuit 210, a processor circuit 220, a user interface 230, and a therapy circuit 240. At least a portion of the system 200 may be implemented in the IMD 102, the WMD 103, or the external system 105 such as one or more of the external device 106 or the remote device 108.

The data receiver circuit 210 may receive physiological information from a patient. In an example, the data receiver circuit 210 may include a sense amplifier circuit configured to sense a physiological signal from a patient via a physiological sensor, such as an implantable, wearable, or otherwise ambulatory sensor or electrodes associated with the patient. The sensor may be incorporated into or associated with an ambulatory device such as the IMD 102 or the WMD 103. In some examples, the physiological signals sensed from a patient may be stored in a storage device, such as an electronic medical record (EMR) system. The data receiver circuit 210 may receive the physiological signal from the storage device, such as in response to a user command or a triggering event.

By way of example and not limitation, and as illustrated in FIG. 2, the data receiver circuit 210 may receive heart sound information 212, cardiac electrical information 214, and activity or posture information 216. The heart sound information 212, which can be sensed using a heart sound sensor from the patient, includes one or more of S1, S2, S3, or S4 heart sound components. In an example, the heart sound information 212 may include a body motion/vibration signal indicative of cardiac vibration, which is correlated to or indicative of heart sounds. In an example, at least one heart sound sensor can be included in the heart failure monitor system 200. Examples of the heart sound sensor may include an accelerometer, an acoustic sensor, a microphone, a piezo-based sensor, or other vibrational or acoustic sensors. The accelerometer can be a one-axis, a two-axis, or a three-axis accelerometer. Examples of the accelerometer may include flexible piezoelectric crystal (e.g., quartz) accelerometer or capacitive accelerometer, fabricated using micro electro-mechanical systems (MEMS) technology. The heart sound sensor may be included in the IMD 102 or the WMD 103, or disposed on a lead such as a part of the lead system associated with the IMD 102 or the WMD 103. In an example, an accelerometer (or other sensors) may sense an epicardial or endocardial acceleration (EA) signal from a portion of a heart, such as on an endocardial or epicardial surface of one of a left ventricle, a right ventricle, a left atrium, or a right atrium. The EA signal may contain components corresponding to various heart sound components such as one or more of S1, S2, S3, or S4 components.

The heart sound information 212 may include the patient's intrinsic heart sounds (i.e., in the absence of cardiac stimulation). Such heart sound information is referred to as baseline heart sound information. In some examples, the heart sound information 212 may be sensed during or immediately after electrostimulation (e.g., cardiac pacing or neurostimulation). In some examples, the heart sound information 212 may be sensed when the patient is in a specific posture (e.g., supine, sitting, standing, or other positions), or when the patient is engaged in a specific type of physical activity or level of exertion (e.g., leg raise, brisk walking, jogging, grocery shopping, or aerobic exercise, among others).

The cardiac electrical information 214 may include, for example, surface electrocardiogram (ECG) sensed from electrodes placed on the body surface, subcutaneous ECG sensed from electrodes placed under the skin, intracardiac electrogram (EGM) sensed from the one or more implantable electrodes. The cardiac electrical information 214 may be sensed via electrodes included in or communicatively coupled to the IMD 102 or the WMD 103. The cardiac electrical information 214 may additionally include heart rate, heart rate variability, cardiac timing parameters, etc., which can be measured or determined from the cardiac electrical information 214.

The activity or posture information 216 may be sensed using an accelerometer configured to sense a physical activity signal. The accelerometer for sensing physical activity may be different from the accelerometer for detecting respiration-induced chest wall or abdominal movement or acceleration. In an example, an accelerometer may be included in a separate device other than the IMD 102 or the WMD 103, such as a smart watch or other wearable devices, to sense physical activity information. The data receiver circuit 210 can be communicate with the separate device and received therefrom the physical activity information. Acceleration signals sensed by the at least one accelerometer may be filtered to a specific frequency band to detect a physical activity level. Posture information may be detected using a posture sensor, which can take the form of a tilt switch or a single- or multi-axis accelerometer. The posture sensor may be disposed external to the body or implanted inside the body. Posture may be represented by, for example, a tilt angle. In some examples, the posture or physical activity information may be derived from thoracic impedance information.

In some examples, the heart sound information 212, the cardiac electrical information 214, and the activity or posture information 216 may be collected substantially concurrently from the same patient. In an example, the heart sound information 212, cardiac electrical information 214, and activity or posture information 216 may be time-aligned to each other. This allows accurate and reliable cross-signal measurement, such as various cardiac timing intervals (e.g., Q-S1 interval between the Q wave on a ECG and the S1 heart sound on a heart sound signal within the same cardiac cycle), or activity-synchronized S1 heart sound component, as described further below.

In addition to the heart sounds, cardiac electrical activities, and physical activity and posture information, the data receiver circuit 210 may receive other physiological or functional information of the patient including, for example, physical activity signal, posture signal, a thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal, physiological response to activity, apnea hypopnea index, one or more respiration signals such as a respiratory rate signal or a tidal volume signal, brain natriuretic peptide (BNP), blood panel, sodium and potassium levels, glucose level and other biomarkers and bio-chemical markers, among others.

The processor circuit 220 may detect a heart failure status in a patient using the received physiological information. The processor circuit 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The processor circuit 220 may include circuit sets comprising one or more other circuits or sub-circuits, including a heart sound analyzer circuit 222 and a heart failure detector circuit 225. These circuits or sub-circuits may, either individually or in combination, perform the functions, methods or techniques described herein. In an example, hardware of the circuit set may be immutably designed to conduct a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to conduct portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The heart sound analyzer circuit 222 can preprocess the heart sound information 212, such as using a filter or a filter bank to remove or attenuate one or more of low-frequency signal baseline drift, high frequency noise, or other unwanted frequency contents. In an example, the heart sound information 212 may be band-pass filtered to a frequency range of approximately 5-90 Hz, or approximately 9-90 Hz. In an example, the filter may include a double or higher-order differentiator configured to calculate a double or higher-order differentiation of the heart sound signal. The heart sound analyzer circuit 222 may detect one or more heart sound components (e.g., S1, S2, S3, or S4) from the preprocessed heart sound signal. The heart sound component can be recognized based on heart sound signal amplitude, power, timing, morphology, spectrum, statistical analysis, or signal complexity analysis (e.g., signal entropy). In some examples, the heart sound analyzer circuit 222 can detect the heart sound components further using the cardiac electrical information 214, such as timings of QRS complex or R wave within a cardiac cycle, heart rates, heart rate variability, etc.

The heart sound analyzer circuit 222 can generate one or more heart sound metrics from the received heart sound information 212 including, for example, an S3 intensity 223 or a heart sound-based cardiac timing interval 224. To measure S3 intensity 223, the heart sound analyzer circuit 222 can detect an S1 heart sound component based on signal amplitude or power within an S1 detection window, and detect am S2 heart sound component based on signal amplitude or power within an S2 detection window. The S1 and S2 detection windows can have user-programmable locations (e.g., the beginning or the end of the detection window) and window lengths. In an example, the S1 detection window may begin at 50 milliseconds (msec) following a detected R wave on an ECG signal and have a duration of 300 msec. The S2 detection window can begin at specified offset following a detected R wave or S1 heart sound. Based on the detection of S1 and/or S2 components, S3 can be determined based on signal amplitude or power within an S3 detection window. In an example, the S3 detection window may begin at the S2 timing, or a specified offset following the detected S2 (e.g., approximately 50-125 msec following the S2 timing). The S3 detection window may have a duration of approximately 125 msec. In some examples, the offset or the S3 window duration may be a function of a physiological variable such as a heart rate. For example, the offset may be inversely proportional to the heart rate, such that the S3 detection window may start at a smaller offset following the S2 at a higher heart rate. Once S3 is detected, S3 intensity can be determined as S3 amplitude or S3 power (e.g., root-mean-squared value of heart sound signal portion around the S3 peak).

The heart sound-based cardiac timing interval 224 may include timing of S1 heart sound relative to a fiducial point. In an example the S1 timing may be characterized by a Q-S1 interval between the onset of the QRS to the S1 heart sound, also known as a pre-ejection period (PEP). The heart sound analyzer circuit 222 may determine the Q-S1 interval using the heart sound information 212 and the cardiac electrical information 214 substantially concurrently collected and time-aligned with the heart sound information 212. Cardiac dyssynchrony can cause prolongation of Q-S1 interval. Such prolongation effect on PEP or Q-S1 interval is more prominent in HFrEF than in HFpEF, the latter generally having normal to non-significant changes in PEP due to preserved LV systolic function. In addition to the Q-S1 interval, the heart sound analyzer circuit 222 may determine other cardiac timing intervals that may be used for detecting heart failure status, particularly for differential diagnoses between HFpEF and HFrEF, or to assess efficacy of a heart failure therapy. By way of non-limiting example, such cardiac timing interval may include a systolic timing interval (STI) representing a time interval from the onset of the QRS complex on the ECG to the S2 heart sound, a left-ventricular ejection time (LVET) representing a time interval between S1 and S2 heart sounds, or a diastolic timing interval (DTI) representing a time interval between the S2 heart sound and the onset of the subsequent QRS complex on the ECG, among others. These heart sound-based cardiac timing intervals may be correlated with cardiac contractility or cardiac diastolic function of the heart. The heart sound metrics may further include composite metrics such as PEP/LVET ratio, STI/DTI ratio, STI/cycle length (CL) ratio, or DTI/CL ratio, among others.

Figure 3:
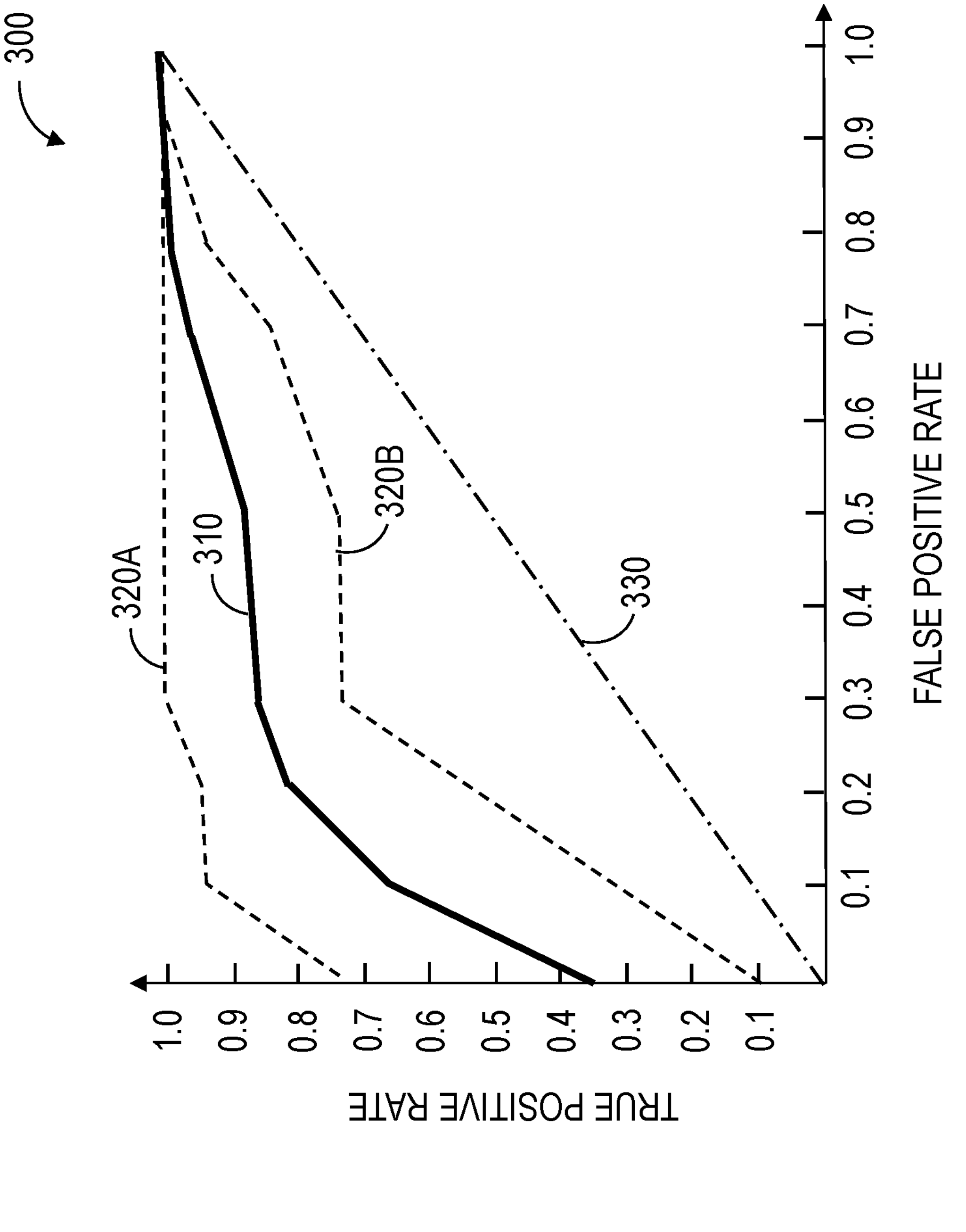
FIG. 3 illustrates and example of a receiver operating characteristic (ROC) curve showing the performance of an S3 intensity-based heart failure classification model that discriminates HFpEF from non-HFpEF controls.

The HF detector circuit 225 can detect a heart failure status using one or more of the S3 intensity 223 or the heart sound-based cardiac timing interval 224. The detection of heart failure status may include detecting a HFpEF 226, a HFrEF 227, or a HFpEF to HFrEF transition 228. In one example, the HF detector circuit 225 can detect HFpEF 226 when the S3 intensity 223 exceeds an S3 intensity threshold ($S3_{TH}$). Referring to FIG. 3, the diagram 300 illustrates a receiver operating characteristic (ROC) curve 310 that shows the performance of an S3 intensity-based heart failure classification model that discriminates HFpEF from non-HFpEF controls based on a comparison of S3 intensity 223 to an S3 intensity threshold ($S3_{TH}$). The S3 intensity is determined using the heart sound analyzer circuit 222 from heart sound signals respectively sensed from a group of patients in a specific posture and resting state. To correct for beat-to-beat or over-time variations in heart sound intensity, the S3 intensity is normalized with respect to the intensity of the immediately preceding S1 intensity within the same cardiac cycle. Each data point on the ROC curve 310 represents a true positive rate (sensitivity, on the y-axis) and false positive rate (1-specificity, on the x-axis) when the classification is made using a particular $S3_{TH}$ value. Also shown in the diagram 300 are 95% confidence intervals between an upper bound ROC curve 320A and a lower bound ROC curve 320B, both of which are well above the chance line 330 (representing a random guess of presence of absence of HFpEF). In this example, the area under the curve (AUC) of the ROC curve 310 is approximately 0.85, suggesting that S3 intensity-based heart failure classification model can offer a high degree of separability between HFpEF and non-HFpEF status.

Figure 4A:
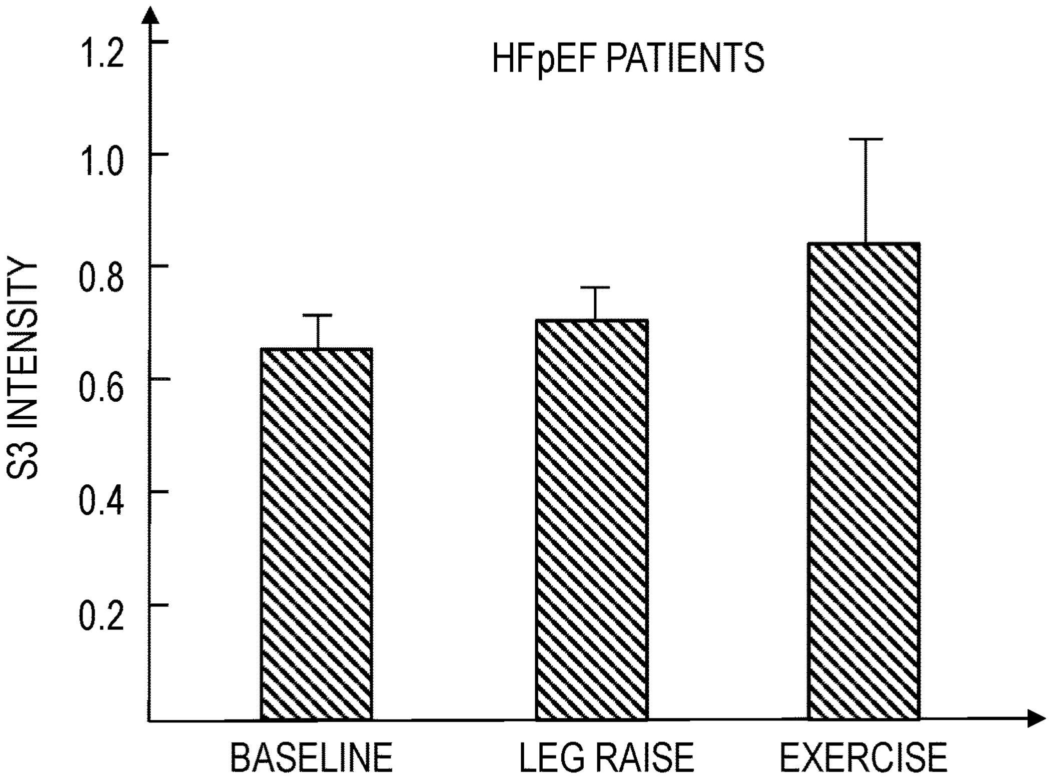
FIG. 4A illustrate by way of example and not limitation S3 intensities detected from a group of HFpEF patients in in a baseline resting state and different activity states.
Figure 4B:
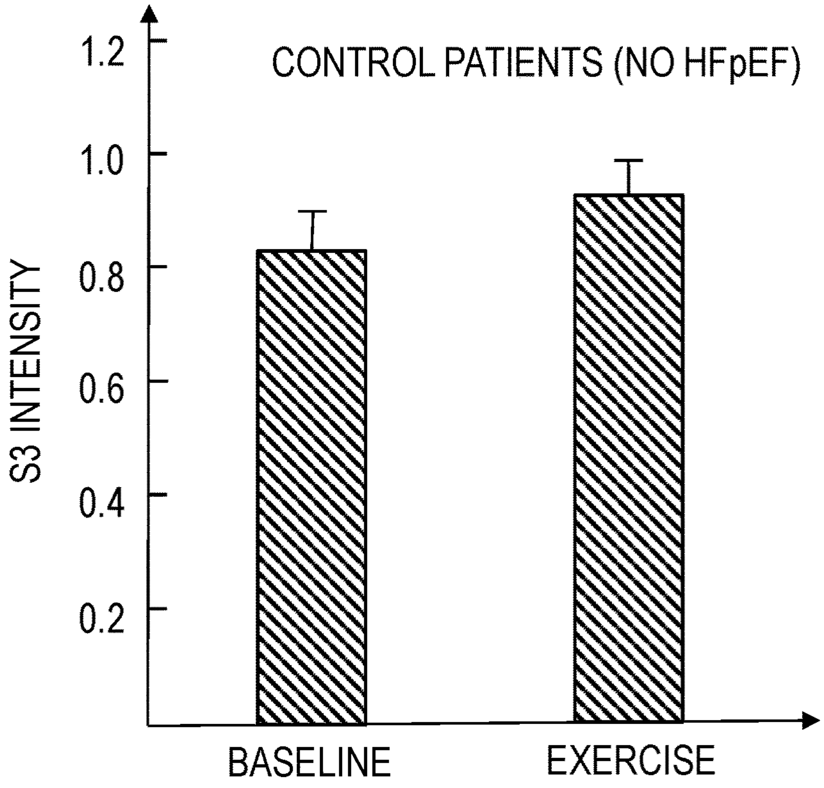
FIG. 4B illustrates by way of example and not limitation S3 intensities detected from a group of control subjects (without HFpEF) in a baseline resting state and exercise state.

In some examples, the heart sound information being used for detecting heart failure status can be collected when the patient is in a specific posture or engaged in a physical activity of certain type or level of exertion (e.g., leg raise, brisk walking, jogging, grocery shopping, aerobic exercise, among others). The HF detector circuit 225 can detect the presence of HFpEF 226 using heart sound metrics (e.g., S3 intensity 223 or the heart sound-based cardiac timing interval 224) derived from respective heart sound signals when the patient is in different postures or engaged in different activities. In an example, the HF detector circuit 225 can detect the HFpEF 226 based at least in part on a change or a rate of change from a first heart sound metric (e.g., a first S3 intensity metric S31) corresponding to a first posture or activity state (e.g., supine or resting state) to a second heart sound metric (e.g., a second S3 intensity metric S32) corresponding to a different second posture or activity state (e.g., exercise of an elevated exertion level). In particular, HFpEF 226 is detected when the difference $\Delta S3=S32-S31$, or the rate of change $\Delta S3/\Delta t$, exceeds respective thresholds, and HFpEF 226 is not detected if $\Delta S3$ or $\Delta S3/\Delta t$ falls below the respective thresholds. Referring to FIGS. 4A-4B, diagram 410 in FIG. 4A illustrates average S3 intensities 412, 414, and 416 detected from heart sound signals over a group of HFpEF patients in a baseline resting state, leg raise state, and exercise state, receptively. For comparison, the diagram 420 in FIG. 4B illustrates average S3 intensities detected from receptive heart sound signals over a group of control subjects (without HFpEF) in a baseline resting state 422 and during exercise 426. The data in this example indicate a trend of more significant increase in S3 intensity ($\Delta S3$) from the baseline resting state to exercise state in HFpEF patients than in control subjects.

The HF detector circuit 225 can perform differential heart failure diagnosis to distinguish HFpEF 226 from HFrEF 227 using metrics such as the heart sound-based cardiac timing interval 224. In an example, the heart sound-based cardiac timing interval 224 may include a Q-S1 interval indicative of a pre-ejection period (PEP). The HF detector circuit 225 can detect the presence of HFrEF in response to Q-S1 interval exceeding a threshold, and detect the presence of HFpEF in response to the Q-S1 interval falling below the threshold. In another example, the heart sound-based cardiac timing interval 224 may include a heart sound-based systolic time interval (STI) between a QRS complex in a cardiac electrical signal and an S2 with a same cardiac cycle. The HF detector circuit 225 can detect the presence of HFrEF in response to the heart sound-based STI falling below a threshold, and detect the presence of HFpEF in response to the heart sound-based STI exceeding the threshold. In another example, the heart sound-based cardiac timing interval 224 may include an S1 to S2 time interval indicative of a left ventricular ejection time (LVET). The HF detector circuit 225 can detect the presence of HFrEF in response to the S1 to S2 time interval falling below a threshold, and detect the presence of HFpEF in response to the S1 to S2 time interval exceeding the threshold. In yet another example, the heart sound-based cardiac timing interval 224 may include a heart sound-based diastolic time interval (DTI) between S2 and a subsequent QRS complex in a cardiac electrical signal. The HF detector circuit 225 can detect the presence of HFrEF in response to the heart sound-based DTI falling below a threshold, and detect the presence of HFpEF in response to the heart sound-based DTI exceeding the threshold.

In some examples, the HF detector circuit 225 may trend the heart sound metric over time, and detect a transition from HFpEF to HFrEF based at least in part on the trended heart sound metric. For example, by trending one or more cardiac timing intervals such as heart sound-based PEP, STI, LVEP, or DTI as described above, the HF detector circuit 225 may detect a transition from HFpEF to HFrEF. The transition from HFpEF to HFrEF may indicate worsening of LV systolic function, in which case a therapy (e.g., drug therapy or electrostimulation therapy) may be initiated or adjusted.

The detected heart failure status (e.g., the HFpEF 226, the HFrEF 227, or the HFpEF-HFrEF transition 228), or a human-perceptible notification of the detection of the heart failure status, may be presented to a user via the user interface 230, such as being displayed on a display screen. Also displayed or otherwise presented to the user via the user interface 230 may include one or more of the sensed physiological signal, signal metrics such as various heart sound metrics as described above, among other intermediate measurements or computations. The information may be presented in a table, a chart, a diagram, or any other types of textual, tabular, or graphical presentation formats. The presentation of the output information may include audio or other media format. In an example, alerts, alarms, emergency calls, or other forms of warnings may be generated to signal the system user about the detected heart failure status.

The optional therapy circuit 240 may be configured to deliver a therapy to the patient in response to the detected heart failure status. Examples of the therapy may include electrostimulation therapy delivered to the heart, a nerve tissue, other target tissues, a cardioversion therapy, a defibrillation therapy, or drug therapy including delivering drug to a tissue or organ. In some examples, the therapy circuit 240 may modify an existing therapy, such as adjust a stimulation parameter or drug dosage.

Although the discussion herein focuses on heart failure detection, this is meant only by way of example but not limitation. Systems, devices, and methods discussed in this document may also be suitable for detecting various sorts of diseases or for assessing risk of developing other worsened conditions, such as cardiac arrhythmias, heart failure decompensation, pulmonary edema, pulmonary condition exacerbation, asthma and pneumonia, myocardial infarction, dilated cardiomyopathy, ischemic cardiomyopathy, valvular disease, renal disease, chronic obstructive pulmonary disease, peripheral vascular disease, cerebrovascular disease, hepatic disease, diabetes, anemia, or depression, among others.

Figure 5:
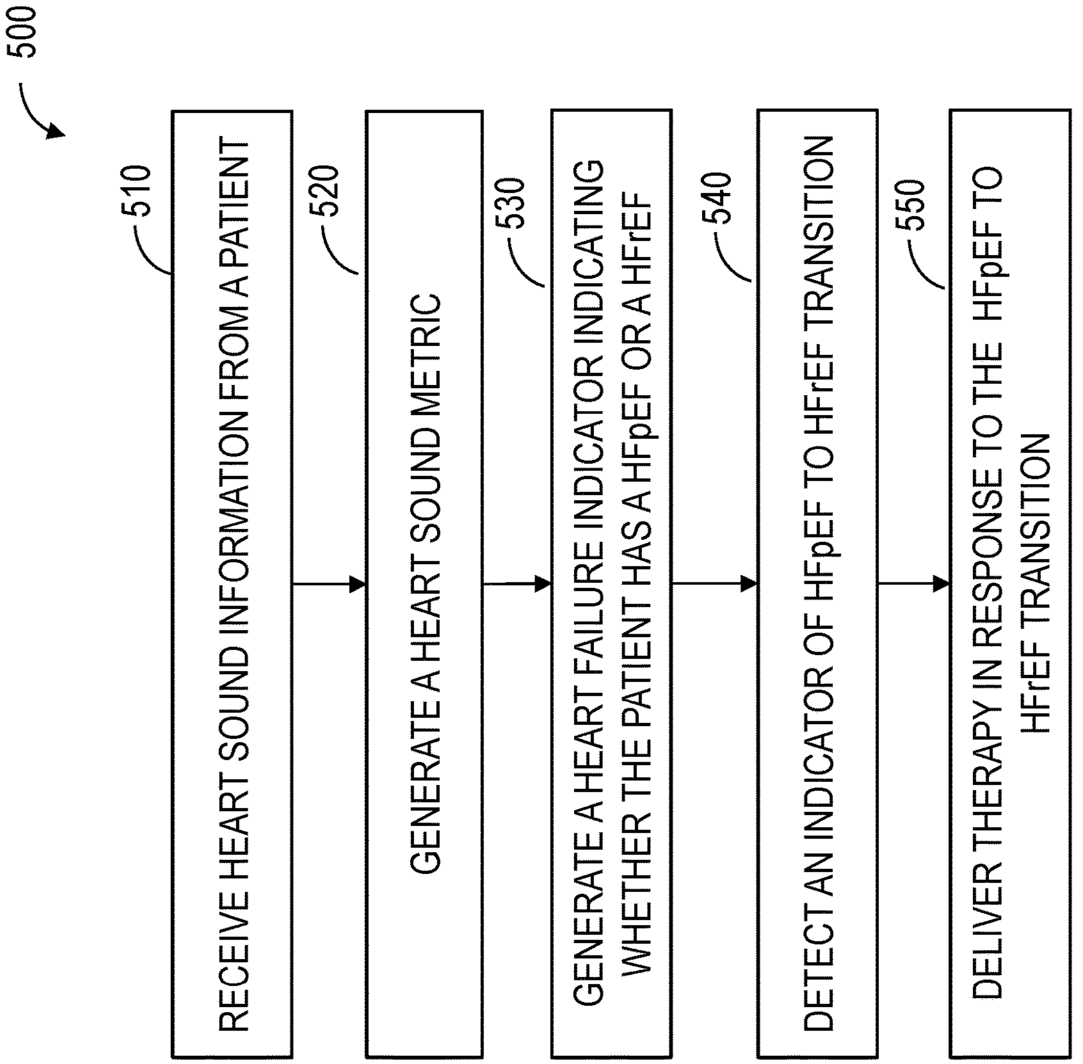
FIG. 5 illustrates generally an example of a method for detecting and managing heart failure in a patient, such as patients with HFpEF or HFrEF.

FIG. 5 illustrates generally an example of a method 500 for detecting and managing heart failure in a patient, such as patients with a heart failure with preserved ejection fraction (HFpEF) or a heart failure with reduced ejection fraction (HFrEF). The method 500 may be implemented and executed in an ambulatory medical device such as an implantable or wearable medical device, or in a remote patient management system. In an example, the method 500 may be implemented in and executed by the IMD 102 or the WMD 103, the external system 105, or the heart failure monitor system 200.

The method 500 begins at 510 to receive physiological information from a patient. The physiological information may include sound information. The heart sound information includes one or more of S1, S2, S3, or S4 heart sound components. The heart sounds may be detected using a sensor associated with or included in an ambulatory or wearable device, such as the IMD 102 or the WMD 103. In some examples, endocardial acceleration signals sensed from inside the heart may be used to analyze heart sounds. The heart sound information may include the patient's intrinsic heart sounds, also referred to as reference or baseline heart sound information, or paced heart sound information that are sensed during or immediately after electrostimulation (e.g., cardiac pacing or neurostimulation). In some examples, the heart sound information may be sensed when the patient is in a specific posture (e.g., supine, sitting, standing, or other positions), or when the patient is engaged in a specific type of physical activity or level of exertion (e.g., leg raise, brisk walking, jogging, grocery shopping, or aerobic exercise, among others).

The received physiological information may additionally include one or more of cardiac electrical information or physical activity or posture information. The cardiac electrical information may include, for example, surface electrocardiogram (ECG) sensed from electrodes placed on the body surface, subcutaneous ECG sensed from electrodes placed under the skin, intracardiac electrogram (EGM) sensed from the one or more implantable electrodes. The activity or posture information may be sensed using an accelerometer configured to sense a physical activity signal. The heart sound information may be sensed substantially concurrently with the cardiac electrical information and/or the activity or posture information, or otherwise time-aligned to the cardiac electrical information and/or the activity or posture information.

At 520, a heart sound metric can be generated from at least the received heart sound information, such as using the heart sound analyzer circuit 222. The heart sound metrics can be based on one or more of the heart sound components (e.g., S1, S2, S3, or S4), optionally further based on other physiological information such as cardiac electrical information. The heart sound metrics can be correlated to the level of cardiac synchrony and indicative of cardiac performance. By way of example and not limitation, the heart sound metric may include one or more of an S3 intensity or a heart sound-based cardiac timing interval, as described above with reference to FIG. 2. The S3 intensity can be determined as S3 amplitude or S3 power (e.g., root-mean-squared value of heart sound signal portion around the S3 peak) within an S3 detection window. The heart sound-based cardiac timing interval may include timing of S1 heart sound relative to a fiducial point, such as a Q-S1 interval between the onset of the QRS to the S1 heart sound, also known as a pre-ejection period (PEP). Other examples of the cardiac timing intervals may include a systolic timing interval (STI) representing a time interval from the onset of the QRS complex on the ECG to the S2 heart sound, a left-ventricular ejection time (LVET) representing a time interval between S1 and S2 heart sounds, or a diastolic timing interval (DTI) representing a time interval between the S2 heart sound and the onset of the subsequent QRS complex on the ECG, among others.

At 530, a heart failure indicator indicating whether the patient has a HFpEF or a HFrEF can be determined based on one or more of the S3 intensity or the heart sound-based cardiac timing interval, such as using the HF detector circuit 225. In one example, an HFpEF can be detected when the S3 intensity exceeds an S3 intensity threshold ($S3_{TH}$). In another example, an HFpEF can be detected based at least in part on a change or a rate of change of a heart sound metric (e.g., the S3 intensity or the heart sound-based cardiac timing interval) when the patient is in different postures or engaged in different activities. For example, in response to the change from a first posture or activity state (e.g., supine or resting state) to a different second posture or activity state (e.g., exercise of an elevated exertion level), an HFpEF is detected when the difference or the rate of change in S3 intensity exceeds respective thresholds, and not detected if the difference or the rate of change in S3 intensity falls below the respective thresholds.

In some examples, a heart sound-based cardiac timing interval determined from step 520 may be used to distinguish HFpEF from HFrEF. In an example, a HFrEF can be detected in response to a Q-S1 interval (indicative of pre-ejection period, or PEP) exceeding a threshold, and a HFpEF can be detected in response to the Q-S1 interval falling below the threshold. In another example, a HFrEF can be detected in response to an QRS to S2 interval (indicative of systolic time interval, or STI) falling below a threshold, and a HFpEF can be detected in response to the QRS to S2 interval exceeding the threshold. In another example, a HFrEF can be detected in response to an S1 to S2 time interval (indicative of a left ventricular ejection time, or LVET) falling below a threshold, and a HFpEF can be detected in response to the S1 to S2 interval exceeding the threshold. In yet another example, a HFrEF can be detected in response to an S2 to subsequent QRS interval (indicative of diastolic time interval, or DTI) falling below a threshold, and a HFpEF can be detected in response to the S2 to subsequent QRS interval exceeding the threshold.

At 540, an indicator of a transition from HFpEF to HFrEF can be detected using the heart failure indicator generated at 530. In some examples, the heart sound metric generated at 520 may be trended over time, and the transition from HFpEF to HFrEF can be detected based at least in part on the trended heart sound metric. For example, by trending one or more cardiac timing intervals such as heart sound-based PEP, STI, LVEP, or DTI as described above, a transition from HFpEF to HFrEF can be detected based on the trend of the heart sound metric.

Figure 6:
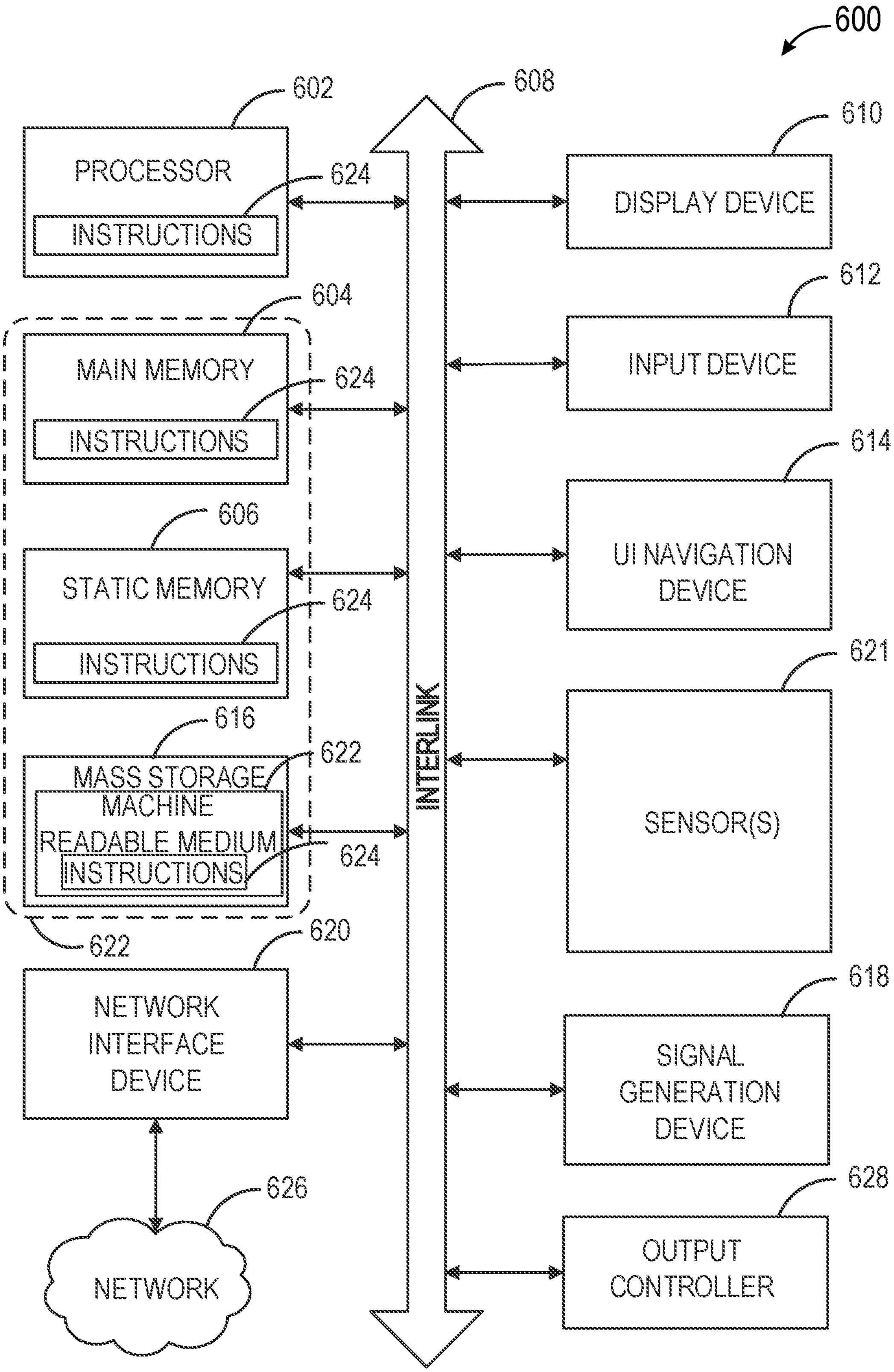
FIG. 6 illustrates generally a block diagram of an example machine upon which any one or more of the techniques discussed herein may perform.

At 550, a therapy may be delivered to the patient based on the detected heart failure status, such as the detected transition from HFpEF to HFrEF. HFrEF may indicate worsening of LV systolic function, in which case a therapy (e.g., drug therapy or electrostimulation therapy) may be initiated or adjusted. Examples of the therapy may include electrostimulation therapy delivered to the heart, a nerve tissue, other target tissues, a cardioversion therapy, a defibrillation therapy, or drug therapy. In some examples, an existing therapy may be modified, such as by adjusting a stimulation parameter or drug dosage. In some examples, the detected heart failure status (e.g., the HFpEF, the HFrEF, or the detected transition from HFpEF to HFrEF, or a human-perceptible notification of the detection of the heart failure status, may be presented to a user such as displayed on a user interface FIG. 6 illustrates generally a block diagram of an example machine 600 upon which any one or more of the techniques (e.g., methodologies) discussed herein may perform. Portions of this description may apply to the computing framework of various portions of the IMD 102, the WMD 103, the external system 105, or the heart failure monitor system 200.

In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may function as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specific operations when operating. In an example, hardware of the circuit set may be immutably designed to conduct a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to conduct portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610 (e.g., a raster display, vector display, holographic display, etc.), an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (GPS) sensor, compass, accelerometer, or other sensor. The machine 600 may include an output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine-readable media.

While the machine-readable medium 622 is illustrated as a single medium, the term "machine readable medium" may include a single medium or multiple media (e.g., a centralized or distributed database, and/or associated caches and servers) configured to store the one or more instructions 624.

The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical-device system for detecting and managing heart failure, the medical-device system comprising:
- a data receiver circuit configured to receive heart sound information sensed from a patient, the heart sound information including one or more of S1, S2, S3, or S4 heart sound components; and
- a heart failure detector circuit configured to:
  - generate a heart sound metric using the received heart sound information; and
  - generate a heart failure indicator indicating whether the patient has a heart failure with preserved ejection fraction (HFpEF) or a heart failure with reduced ejection fraction (HFrEF) based at least in part on the generated heart sound metric.

2. The medical-device system of claim 1, comprising a wearable device that includes an accelerometer and the heart failure detector circuit, the accelerometer configured to sense the heart sound information from the patient.

3. The medical-device system of claim 2, wherein the heart sound metric includes an S3 intensity metric,
- wherein the heart failure detector circuit configured to generate the heart failure indicator indicating a presence of HFpEF when the S3 intensity metric exceeds an S3 threshold.

4. The medical-device system of claim 3, wherein the data receiver circuit is configured to receive the heart sound information sensed from the patient when the patient is in a specific posture or engaged in a specific physical activity, the medical-device system comprising:
- at least one of a posture sensor configured to detect the specific posture in the patient, or an activity sensor configured to detect the patient engagement in the specific physical activity.

5. The medical-device system of claim 4, wherein the received heart sound information includes first heart sound information when the patient is in a resting state and second heart sound information when the patient in a physically active state,
- wherein the heart failure detector circuit is configured to:
  - generate a first S3 intensity metric from the first heart sound information and a second S3 intensity metric from the second heart sound information; and
  - generate the heart failure indicator indicating a presence of HFpEF based at least in part on a change or a rate of change from the first S3 intensity metric to the second S3 intensity metric.

6. The medical-device system of claim 1, wherein the heart sound metric includes an S1 timing relative to a fiducial point, the S1 timing indicative of a pre-ejection period,
- wherein the heart failure detector circuit is configured to generate the heart failure indicator indicating (i) a presence of HFrEF in response to the S1 timing relative to the fiducial point exceeding a threshold, and (ii) a presence of HFpEF in response to the S1 timing relative to the fiducial point falling below the threshold.

7. The medical-device system of claim 6, wherein the data receiver circuit is further configured to receive cardiac electrical activity information,
- wherein the heart failure detector circuit is configured to recognize, from the received cardiac electrical activity information, the fiducial point using a QRS complex within a cardiac cycle preceding the S1 component.

8. The medical-device system of claim 1, wherein the heart sound metric includes a heart sound-based systolic time interval between a QRS complex in a cardiac electrical signal and an S2 heart sound component with a cardiac cycle,
- wherein the heart failure detector circuit is configured to generate the heart failure indicator indicating (i) a presence of HFrEF in response to the heart sound-based systolic time interval falling below a threshold, and (ii) a presence of HFpEF in response to the heart sound-based systolic time interval exceeding the threshold.

9. The medical-device system of claim 1, wherein the heart sound metric includes an S1 to S2 time interval indicative of a left ventricular ejection time,
- wherein the heart failure detector circuit is configured to generate the heart failure indicator indicating (i) a presence of HFrEF in response to the S1 to S2 time interval falling below a threshold, and (ii) a presence of HFpEF in response to the S1 to S2 time interval exceeding the threshold.

10. The medical-device system of claim 1, wherein the heart sound metric includes a heart sound-based diastolic time interval between S2 and a subsequent QRS complex in a cardiac electrical signal, wherein the heart failure detector circuit is configured to generate the heart failure indicator indicating (i) a presence of HFrEF in response to the heart sound-based diastolic time interval falling below a threshold, and (ii) a presence of HFpEF in response to the heart sound-based diastolic time interval exceeding the threshold.

11. The medical-device system of claim 1, wherein the heart failure detector circuit is configured to generate a trend of the heart sound metric over time, and to detect an indicator of HFpEF to HFrEF transition based at least in part on the trended heart sound metric.

12. The medical-device system of claim 1, comprising a therapy circuit configured to initiate or adjust a heart failure therapy in response to the detected indicator of HFpEF to HFrEF transition.

13. A method of detecting and managing heart failure using a medical-device system, the method comprising:

receiving heart sound information sensed from a patient, the heart sound information including one or more of S1, S2, S3, or S4 heart sound components;

generating a heart sound metric using the received heart sound information; and generating a heart failure indicator indicating whether the patient has a heart failure with preserved ejection fraction (HFpEF) or a heart failure with reduced ejection fraction (HFrEF) based at least in part on the generated heart sound metric.

14. The method of claim 13, wherein the heart sound metric includes an S3 intensity metric, wherein generating the heart failure indicator includes an indicator indicating a presence of HFpEF when the S3 intensity metric exceeds an S3 threshold.

15. The method of claim 13, comprising:

sensing a posture or a physical activity state of the patient using an ambulatory sensor; and sensing the heart sound information using an accelerometer when the sensed posture or the sensed physical activity satisfies a condition.

16. The method of claim 15, wherein sensing the heart sound information includes sensing first heart sound information when the patient is in a resting state and sensing second heart sound information when the patient in a physically active state, wherein generating the heart sound metric includes generating a first heart sound metric from the first heart sound information and a second heart sound metric from the second heart sound information, wherein generating the heart failure indicator is based at least in part on a change or a rate of change from the first heart sound metric to the second heart sound metric.

17. The method of claim 16, wherein the first heart sound metric includes a first S3 intensity metric when the patient is in the resting state, and the second heart sound metric includes a second S3 intensity metric when the patient in the physically active state, wherein generating the heart failure indicator includes an indicator indicating a presence of HFpEF in response to a difference between the first and the second S3 intensity metrics exceeding a threshold.

18. The method of claim 13, wherein the heart sound metric includes a cardiac timing interval representing at least one of a pre-ejection period, a systolic time interval, a left ventricular ejection time, or diastolic time interval, wherein generating the heart failure indicator includes an indicator indicating a presence of HFpEF or a presence of HFrEF based on a comparison of the cardiac timing interval to a threshold.

19. The method of claim 13, comprising:

detecting an indicator of HFpEF to HFrEF transition based at least in part on a trend of the heart sound metric; and initiating or adjusting a heart failure therapy in response to the detected indicator of HFpEF to HFrEF transition.

20. A medical-device system for improving heart failure management, including detecting transition from heart failure with preserved ejection fraction (HFpEF) to heart failure with reduced ejection fraction (HFrEF), the medical-device system comprising:

a data receiver circuit configured to receive heart sound information sensed from a patient, the heart sound information including one or more of S1, S2, S3, or S4 heart sound components; and a heart failure detector circuit configured to:

generate a heart sound metric using the received heart sound information, wherein the heart sound metric includes an S1 timing relative to a fiducial point, generate a trend of the heart sound metric over time to monitor disease progression of the patient over time; and detect a transition of an indication from HFpEF to HFrEF based at least in part on the generated trend of the heart sound metric.

* * * * *